(12) United States Patent
Lee et al.

(10) Patent No.: US 11,506,580 B2
(45) Date of Patent: Nov. 22, 2022

(54) SAMPLE SEPARATION DEVICE BASED ON PAPER FOLDING

(71) Applicant: CALTH. Inc., Seongnam (KR)

(72) Inventors: Jeong Hoon Lee, Seongnam (KR); Kyung Jae Lee, Seoul (KR); Sung Il Han, Seoul (KR)

(73) Assignee: CALTH. Inc., Seongnam (KR)

( * ) Notice: Subject to any disclaimer, the term of this patent is extended or adjusted under 35 U.S.C. 154(b) by 833 days.

(21) Appl. No.: 16/337,839

(22) PCT Filed: Aug. 22, 2017

(86) PCT No.: PCT/KR2017/009121
§ 371 (c)(1),
(2) Date: Mar. 28, 2019

(87) PCT Pub. No.: WO2018/062686
PCT Pub. Date: Apr. 5, 2018

(65) Prior Publication Data
US 2020/0041392 A1    Feb. 6, 2020

(30) Foreign Application Priority Data

Sep. 28, 2016 (KR) .................. 10-2016-0124951
Aug. 22, 2017 (KR) .................. 10-2017-0105825

(51) Int. Cl.
*G01N 1/40* (2006.01)
*G01N 27/333* (2006.01)
*G01N 33/48* (2006.01)

(52) U.S. Cl.
CPC ............ *G01N 1/40* (2013.01); *G01N 27/333* (2013.01); *G01N 33/48* (2013.01)

(58) Field of Classification Search
CPC ......... G01N 1/40; G01N 27/333; G01N 33/48
See application file for complete search history.

(56) References Cited

U.S. PATENT DOCUMENTS

| 2013/0128036 A1 | 5/2013 | Whitesides et al. |
| 2016/0146755 A1 | 5/2016 | Crooks et al. |

FOREIGN PATENT DOCUMENTS

| CN | 102311914 A | 1/2012 |
| CN | 104483360 A | 4/2015 |
| JP | 2003066005 A | 3/2003 |
| JP | 2006094822 A | 4/2006 |
| JP | 2008509406 A | 3/2008 |
| JP | 2012504233 A | 2/2012 |
| KR | 20100113393 A | 10/2010 |

(Continued)

OTHER PUBLICATIONS

Li, Xiang, Long Luo, and Richard M. Crooks. "Low-voltage paper isotachophoresis device for DNA focusing." Lab on a Chip 15.20 (2015): 4090-4098. (Year: 2015).*

(Continued)

*Primary Examiner* — Robert J Eom (57) ABSTRACT

The present exemplary embodiments provide a sample separation device which applies an electric field to a selective ion permeable layer based on origami to concentrate a target material in a specific area and concentrates a target material and separates a non-target material through a filter layer in which a paper is compressed to adjust a size of micro pore.

14 Claims, 8 Drawing Sheets

(56) References Cited

FOREIGN PATENT DOCUMENTS

| KR | 20100128340 A | 12/2010 |
|---|---|---|
| KR | 20150095137 A | 8/2015 |
| KR | 20160066891 A | 6/2016 |
| KR | 1020160066891 A | 6/2016 |
| KR | 20160097639 A | 8/2016 |
| KR | 20170082843 A | 7/2017 |

OTHER PUBLICATIONS

Search Report dated Mar. 12, 2020 for European Application No. 17856572.7.
Luo et al., "Low-Voltage Origami-Paper-Based Electrophoretic Device for Rapid Protein Separation," American Chemical Society, Dec. 2, 2014, vol. 86, pp. 12390-12397.
Phan et al., "Sample concentration in a microfluidic paper-based analytical device using ion concentration polarization," Jan. 1, 2016, 10 pages, vol. 222, ISBN:0925-4005, Elsevier B.V.
International Search Report issued in related PCT Application No. PCT/KR2017/009121 dated Jan. 24, 2018.

\* cited by examiner

SAMPLE SEPARATION DEVICE BASED ON PAPER FOLDING

This application is a U.S. National Stage of PCT/KR2017/009121, filed Aug. 22, 2017, which claims the benefit of Korean Patent Application Nos. 10-2016-0124951, filed on Sep. 28, 2016 and 10-2017-0105825, filed on Aug. 22, 2017 in the Korean Intellectual Property Office.

TECHNICAL FIELD

The technical field of the present exemplary embodiment relates to a biological sample separation device which is capable of concentrating a target material in a specific section and being manufactured at a low cost. The present invention corresponds to a result of a research project (development of a paper-based molecular sieving mechanism and a solution for acute disease) supported by National Research Foundation of Korea with funds of the government (the Ministry of Education) in 2016 (Project No. 1345256126).

BACKGROUND ART

The contents described in this section merely provide background information on the present exemplary embodiment but do not constitute the related art. Modern medicine aims not to simply extend the lifespan, but to prolong the healthy life. Therefore, a paradigm of the future medicine is changing to implement 3P of preventive medicine, predictive medicine, and personalized medicine, rather than focusing on the therapeutic medicine. In order to specifically realize the paradigm, early identification and early treatment of diseases have become important means and to this end, studies on a biomarker are actively being carried out.

A biomarker refers to an indicator which identifies a normal or abnormal state or predicts a therapeutic reaction, or is objectively measurable. As the biomarker, nucleic acids such as DNA or RNA (gene), protein, lipid, metabolite, and a change of a pattern thereof are used. That is, not only a simple material such as blood glucose for diagnosis of diabetes but also genes such as BCR-ABL gene fusion of chronic myelogenous leukemia which is a therapeutic target of Gleevec are biomarkers which are actually used in the clinical fields.

DNA (deoxyribonucleic acid) is a genetic material in the nucleus and a gene is a place where chemical information determining a type of protein created by an organism is stored. Information configuring human body is identified by analyzing DNA and various DNA analysis techniques have been studied, developed, and utilized for prevention and treatment of disease. In order to analyze the diseases using DNA, a gene amplification technique called polymerase chain reaction (PCR) is used. According to the PCR, in order to use a single strand obtained by continuously separating a double helix of DNA as an original for creating a new double helix, heating and cooling are repeated with a heat-stable DNA polymerase. Therefore, the DNA is heated to be separated into two strands. When a short DNA called "primer" is added thereto to be cooled, the primer binds to the DNA. When an enzyme called DNA polymerase is added thereto, the primer part becomes a starting point to replicate the DNA. The DNA is doubled by one cycle of heating and cooling. When the cycle of heating and cooling is repeated dozens of times, DNA may be multiplied billions of times in approximately one hour.

Protein is a complex molecule made up of relatively simple molecules called amino acids, which are generally very large in molecular weight. There are about twenty kinds of amino acids which form the protein and the amino acids are bonded together by chemical bonds to create polypeptide. In this case, the bonds of amino acids are called peptide bonds and are referred to as a polypeptide in the sense that there are many (poly) peptide bonds. In a broad sense, a protein may also be called a polypeptide and generally speaking, when a molecular weight is relatively small, it is called a polypeptide and when a molecular weight is very large, it is called a protein. Such a protein is a representative molecule that constitutes a body of an organism and is a material which serves as a catalyst for various chemical reactions in cells and takes charge of immunity. The protein is a very important organic matter which constitutes a living organisms and participates in in vivo reactions and energy metabolism.

The DNA or the protein is analyzed to determine generation and progression of cancer or disease. Specifically, for the early diagnosis and treatment of intractable diseases such as cancers, a blood fingerprint analysis technique which finds an indicator protein showing a minute changes in an initial stage where a normal cell in the protein included in the blood is developed to a cancer cell is known. The blood fingerprint analysis is a technique which comprehensively analyzes mass spectrometric data of metabolites present in the blood of cancer patients to diagnose the cancer through changing patterns, by taking into account that metabolites of the human body can change depending on the presence or absence of cancer. The blood fingerprint analysis is advantageous in that the cancer is diagnosed immediately from the blood so that the information is promptly achieved.

However, since the current techniques and devices for protein analysis use nano technology, it is difficult to manufacture the devices and the devices are relatively expensive, so that it is difficult to propagate the devices. Further, there is disadvantages in that a high sensitive sensor is necessary for a protein analysis device or it is difficult to precisely analyze with a small amount of sample. In the meantime, recently, in accordance with the development of a nano technology and micro electro mechanical systems (MEMS) technique, it is possible to promptly separate and purify a necessary material only with a small amount of sample by patterning a single fluidics with a nano structure. Further, efforts are actively made to apply these techniques to biotechnology and medical engineering fields. Further, the developed MEMS/NEMS techniques allow the nano structure to be precisely patterned in a desired location with a several nanometers of error tolerances and these techniques are combined with a micro fluidic channel to be actively studied as micro total analysis system (m-TAS) or Lab-on-a-chip.

Specifically, a method which implements a biomolecule concentration and separation apparatus capable of improving a detection accuracy by concentrating biomolecules even in a small amount of sample using glass or other heavy and expensive material is known. According to this method, a film is formed so as to concentrate a target material in a predetermined location while diffusing a material to be analyzed through a narrow pipe or a thin plate. However, these methods have problems in that it is difficult to manufacture the concentration and separation device or it is costly and the device is large and heavy or inconvenient in handling.

DISCLOSURE

Technical Problem

A main object of the exemplary embodiments of the present invention is to provide a biological sample separation device which is manufactured at a low cost by applying an electric field to a selective ion permeable layer based on origami to concentrate and separate a target material in a specific area.

Another object of the exemplary embodiment of the present invention is to concentrate a target material (collection object) in a desired location and separate a non-target material (separation object) through a filter layer in which papers are compressed to adjust a size of micro pore.

Other and further objects of the present disclosure which are not specifically described can be further considered within the scope easily deduced from the following detailed description and the effect.

Technical Solution

According to an aspect of the present exemplary embodiment, a sample separation device includes: a base which is folded with a predetermined interval and includes a plurality of base units which serves as a basic unit to be folded, a coating layer which is located in at least a partial area of the base to prevent the adsorption of a sample to be processed and separate a storage space or a movement path, a plurality of reservoirs which has an area defined by the coating layer and located in each base unit and adsorbs and stores at least a part of a target material to be separated which is included in a sample to be measured or a separation target material excluding the target material from the sample or provides a movement path, and a selective ion permeable layer which at least partially overlaps at least some of reservoirs and selectively transmits ions.

According to another aspect of the present exemplary embodiment, a sample separation device includes: a base which includes a plurality of base units and is formed such that the plurality of base units is folded, a coating layer which is located in at least a partial area of the base to prevent the adsorption of a sample and separate a storage space or a movement path, a plurality of reservoirs which has an area set by the collating layer, is located in the plurality of base units, and stores or moves a collection object to be separated from the sample or a separation object excluding the collection object included in the sample, a selective ion permeable layer which is coupled to some reservoirs of the plurality of reservoirs to selectively transmit ions, and a filter layer which is located in the middle of a movement path of the collection object formed by folding the plurality of base units to filter the separation object.

Advantageous Effects

As described above, according to the exemplary embodiments of the present invention, an electric field is applied to a selective ion permeable layer based on origami to concentrate and separate a target material in a specific area to manufacture the device at a low cost.

According to the exemplary embodiments of the present invention, a target material is concentrated and separated in a desired location through a filter layer in which a paper are compressed to adjust a size of micro pore.

Even if the effects are not explicitly mentioned here, the effects described in the following specification which are expected by the technical features of the present disclosure and their potential effects are handled as described in the specification of the present disclosure.

BEST MODE

Hereinafter, in the description of the present disclosure, a detailed description of the related known functions will be omitted if it is determined that the gist of the present disclosure may be unnecessarily blurred as it is obvious to those skilled in the art and some exemplary embodiments of the present disclosure will be described in detail with reference to exemplary drawings.

Figure 1:
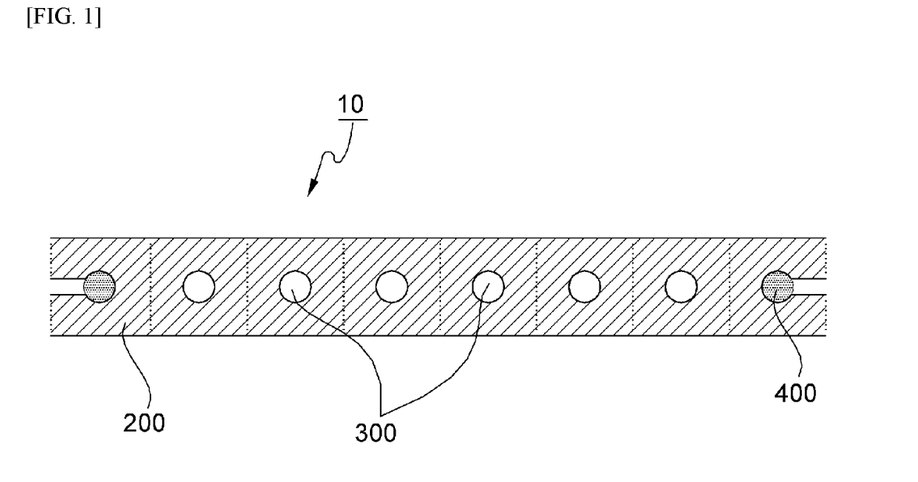
FIGS. 1 to 3 are plan views of a biological sample separation device according to exemplary embodiments of the present invention.

FIG. 1 illustrates a biological sample separation device according to an exemplary embodiment of the present invention.

In order to easily analyze the biological sample, a biological sample separation device according to the present exemplary embodiment concentrates a target material and separates a separation object using separation in accordance with the difference in physical properties of a component. Here, the difference in physical properties is a concept including a mobility, a mass, a charge, and a size. During the separation process, ion concentration polarization is generated using characteristics of electrophoresis and electro osmosis flow to concentrate and separate the sample. Reaction for a concentrated target material obtained as the result may be determined by emission spectroscopy such as inductively coupled plasma (ICP). Specifically, in the present invention, a biomarker in a whole blood of several ng or less may be concentrated several thousand times or more so that the reaction may be determined even by the naked eye and early disease detection and diagnosis are possible. The target material includes protein, nucleic acids (DNA or RNA), steroid, cholesterol, and exosome. However, these are merely examples and it is not limited thereto. Therefore, a sample including an appropriate material depending on a design of the sample separation device to be implemented may be used.

As illustrated in FIG. 1, the biological sample separation device 10 according to the exemplary embodiment of the present disclosure includes a base 100, a coating layer 200, a reservoir 300, and a selective ion permeable membrane 400.

The base 100 may be folded with a predetermined interval and includes a plurality of base units which serves as a basic unit to be folded. The base 100 includes a material having at least a partial fiber texture and the coating layer 200 is coupled to the base 100. The space where the selective ion permeable layer 400 is formed at least partially include a space where the coating layer 200 is not formed and the sample or the target material moves through the space.

In the present exemplary embodiment, even though an example that uses a paper as the base 100 is suggested, the type of the base 100 is not limited thereto and polyethylene terephthalate (PET) may also be used. Specifically, the base 100 may be formed of a material having a structure which is combined with a hydrophobic material or to which a hydrophobic material is permeable.

When a paper is used, a cost is low and elasticity and moldability are good. Further, the coating layer 200 having a predetermined thickness may be easily formed on the paper by adsorbing and impregnating with the hydrophobic material and the binding force with a hydrophobic coating material is excellent. The coating layer is advantageous to store a sample and form a channel through which a predetermined component moves.

The paper is a hydrophilic material configured as a fiber type and depending on the fiber structure, a capillary is formed. When the liquid is dropped thereon, the liquid moves by the capillary phenomenon. That is, when the capillary phenomenon is used, the liquid moves without separately providing a power from the outside and when such a drag force is used, it is easy to move a component differentiated for concentration of the biomolecule. In addition to the paper, other material known as a fiber type hydrophilic material is also used like the paper.

Further, according to another exemplary embodiment of the present invention, when the concentration is progressed, if the material is concentrated to some extends, a concentration plug may slowly move. In this case, if the drag force is reversely applied, it is very helpful to improve a concentration ratio. When the drag force is used for the capillary phenomenon, it is very effective because the concentration may be progressed without using additional power.

The coating layer 200 is located in at least a partial area of the base to prevent the adsorption of a sample to be processed and separate a storage space or a movement path.

In the present exemplary embodiment, a representative example of a hydrophobic material may include alcohol fatty acid ester such as wax. In this case, the wax is printed on the base 100 or heated to be bonded with the base 100. However, it is not limited thereto and may include a component selected from acrylics, olefins, amides, imides, styrenes, carbonates, vinyl acetals, dienes, vinyls, esters, vinyl esters, ketones, fluorocarbons or teflon, PDMS, and silanes. In addition, alkyl silane series silicide, and silicone series such as hydride terminated polydimethylsiloxane (methylhydrosiloxane-dimethysiloxane copolymer) may be included.

Generally, if a substance becomes hydrophobic in a material, it may have hydrophobicity due to the influence of the structure of the surface in contact with water and the influence of the properties of the surface of the material itself. Specifically, the case when the micro channel 20 is formed by coating the paper serving as a base corresponds to the latter. The channel is formed by coating the paper with wax to hydrophilize other parts except a part used as a channel in the paper. Effects similar to the hydrophilic property may also be obtained when a fiber material similar to the paper is used as the base so that a fiber series base may also be used as well as a cellulose paper.

As illustrated in the drawing, the reservoirs 300 includes reservoirs 310 to 340. Areas of the reservoirs are defined by the coating layer and the reservoirs are located in each base unit and adsorb and store at least a part of a target material to be separated which is included in a sample to be measured or a separation object excluding the target material from the sample and provide a movement path. Each reservoir 300 may be implemented to have a circular shape as illustrated in the drawing and also implemented to have various shapes such as a triangular shape, a rectangular shape, and a pentagram. However, the shapes of the reservoirs 300 included in each base unit are not necessarily the same.

The reservoirs 300 may provide a path through which a wet sample, for example, a protein sample to be analyzed or a conductive liquid (buffer) is stored or moves.

According to the exemplary embodiment of the present invention, the reservoirs 300 may be implemented as a space which is exposed without being coupled to the coating layer 200, on at least one surface of the base 100.

The above-described reservoirs 300 are physical spaces formed by the coating layer 200 located on the base 100 and in the present exemplary embodiment, a method of coating a pattern of a hydrophobic material on a paper is disclosed as a method of binding wax which is a hydrophobic material to the base 100. The wax patterning method is not specifically limited so that the paper and the hydrophobic material are simply bonded or the hydrophobic material is impregnated into the paper to be bonded. Desirably, the hydrophobic material is bonded to be impregnated to prevent the leakage of the sample. When a paper is used, a cost is low and elasticity and moldability are good. Further, the coating layer having a predetermined thickness may be easily formed on the paper by adsorbing and impregnating with the hydrophobic material and the binding force with a hydrophobic coating material is excellent.

The base 100 may include porous membrane and a resolution indicating a degree of separating and concentrating the sample may be controlled by adjusting the thickness of the base 100. When the base 100 is a paper, different thicknesses of the paper such as 50 µm, 180 µm, and 350 µm are applied to adjust the resolution and a size of a micro pore of the base 100 is adjusted to control the efficiency of electrophoresis (EP).

According to the exemplary embodiment of the present invention, a sample or a buffer which is a target to be processed is previously injected (pre-wetted) in the reservoir 300 and the base 100 is folded to perform the separation. According to another exemplary embodiment, the material is not previously injected (un-wetted) in the reservoir 300 of the base 100 and the sample or the buffer which is a target to be processed is injected in a slip layer reservoir 630 of a separate slip layer unit 600 to be inserted into a specific section of the folded base 100 or injected in an injection reservoir 153 of an injection base unit 150 and the base is folded to perform the separation.

The selective ion permeable layer 400 at least partially overlaps at least some of the plurality of reservoirs to selectively transmit ions. The patterned selective ion permeable layer 400 serves as a nano filter which selectively transmits protons.

The selective ion permeable membrane 400 may be formed as a Nafion membrane having a predetermined thickness and a predetermined area according to a pattern which is directly predetermined on an adhesive layer 20 using a micro flow patterning or pipetting technique.

Here, even though the method of patterning the selective ion permeable material is not specifically limited, as a method for increasing a concentration efficiency of the target material in the micro channel and controlling a concentration ratio, existing printing techniques (for example, inkjet printing) may be desirably used to form the selective ion permeable material. However, in order to provide a biological sample separation device 10 which is easily manufactured with a low cost, a previously formed Nafion membrane is cut to form a pattern and is attached to the base 100. The selective ion permeable membrane 400 may be formed to have a thickness of several hundreds of nanometers to tens of micrometers and may be formed to have a rectangular pattern having a width of tens to hundreds of micrometers. The selective ion permeable layer 400 may be implemented by a polyelectrolyte such as polystyrene sulfonate (PSS) or polyallylamine hydrochloride (PAH) as well as Nafion and also may be implemented by any material through which the ion is selectively transmitted.

The selective ion permeable membrane 400 is a film which selectively transmits a specific ion material and is a component for implementing a nano channel which functions as a nano filter. For example, the selective ion permeable membrane 400 may serve as a nano filter which selectively transmits protons. When the selective ion permeable layer 400 is implemented by Nafion, H+ ion may be rapidly and selectively transmitted by hopping and vehicle mechanism, due to $SO^{3-}$ of a chemical structure of Nafion. Therefore, the selective ion permeable layer 400 may perform a function of a nano filter.

According to the exemplary embodiment of the present invention, in order to easily separate and concentrate the sample and to maximize the effect of the sample separation by a potential difference, the selective ion permeable layer 400 is coupled to the reservoir 300 located in the base unit adjacent to the end of the base 100.

Figure 2:
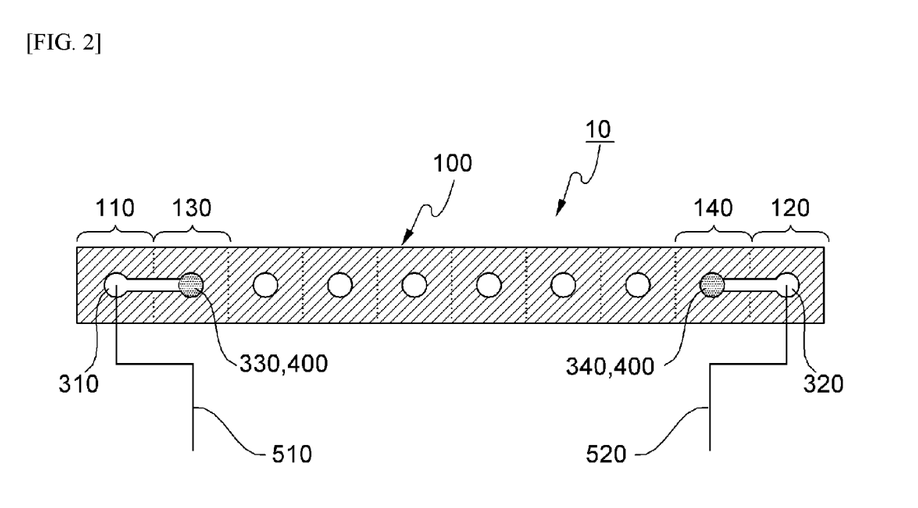

FIG. 2 illustrates a plan view of a biological sample separation device 10 according to an exemplary embodiment of the present invention. FIG. 2 will be described with reference to FIG. 1.

A first end base unit 100 is a base unit located at one end among base units which configure the base 100 and a second end base unit 120 is a base unit located at the other end. The first and second end base units 110 and 120 may perform a function of applying a voltage and supporting the base when the base 100 is folded to perform the separation of the sample.

The coating layer 200 including a hydrophobic material is applied or cut to be attached to the first end base unit 110 and the first end base unit 110 includes the first end reservoir 310 which is an area divided by the coating layer 200 and a first electrode 510 which applies a voltage to the base 100 to cause the separation and the concentration of the sample.

The coating layer 200 including a hydrophobic material is applied or cut to be attached to the second end base unit 120 and the second end base unit 120 includes the second end reservoir 320 which is an area divided by the coating layer 200 and a second electrode 520 which applies a voltage to the base 100 to cause the separation and the concentration of the sample.

A third end base unit 130 is a base unit adjacent to the first end base unit 110 and a fourth end base unit 140 is a base unit adjacent to the second end base unit 120.

The third end reservoir 330 is located in the third end base unit 130 and is connected to the first end reservoir 310. The fourth end reservoir 340 is located in the fourth end base unit 140 and is connected to the second end reservoir 320. The third and fourth end reservoirs 330 and 340 are connected to the selective ion permeable layer 400 to cause the ion selective transmission.

The connection means that there is a channel to which the coating layer 200 is not applied or cut to be attached, between both reservoirs. The sample or the buffer may move between the connected reservoirs 300 by the capillary phenomenon.

As an exemplary embodiment of the present invention, in order to generate a potential difference between the first end reservoir 310 and the second end reservoir 320, a positive electrode, a negative electrode, and a ground may be connected thereto. Further, the potential difference is generated at both ends of the selective ion permeable layer 400 located in the third end reservoir 330 connected to the first end reservoir 310 and the fourth end reservoir 340 connected to the second end reservoir 320 so that the sample may be separated or concentrated by the ion concentration polarization (ICP).

Figure 3:
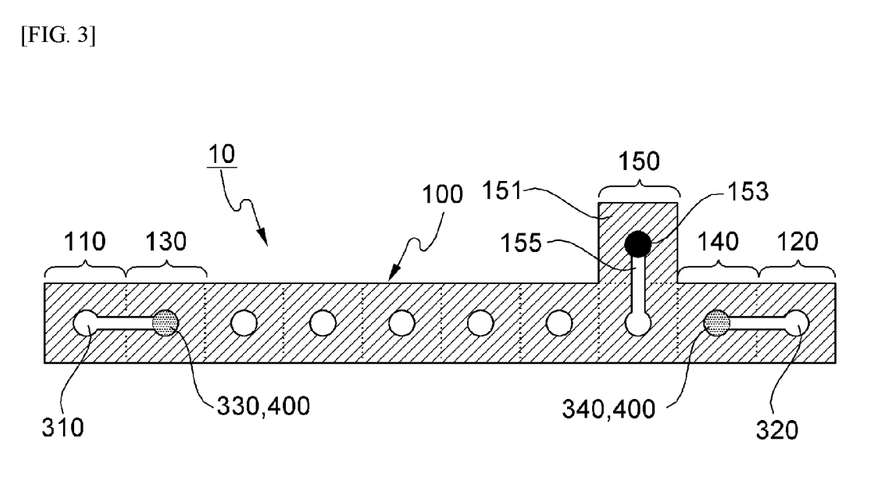

FIG. 3 illustrates a plan view of a biological sample separation device 10 according to an exemplary embodiment of the present invention. FIG. 3 will be described with reference to FIGS. 1 and 2.

An injection base unit 150 includes an injection base unit coating layer 151, an injection reservoir 153, and an injection channel 155.

The injection base unit 150 is directly connected to the base unit, rather than the first to fourth end base units 110, 120, 130, and 140 and when the base 100 is folded, at least a part of the injection base unit is located in the outside.

The injection base unit coating layer 151 is located in at least a partial area of the injection base unit to prevent adsorption of a sample to be processed and separate a storage space or a movement path.

In the injection base unit 150, the coating layer 200 which prevents the adsorption of the sample or the buffer may be located to be at least partially applied or cut to be attached thereto. The injection reservoir 153 as a reservoir and the injection channel 155 which connects the reservoir of the connected base unit and the injection reservoir 153 and serves as a movement path of the sample to be processed may be located as a space separated by the coating layer 151.

According to the exemplary embodiment of the present invention, the injection reservoir 153 and the injection channel 155 are not coupled to the coating layer 200, but may be implemented as at least one surface of the exposed base 100.

The injection base unit 150 has a purpose of injecting a sample to be processed or a buffer to wet the reservoir. As an exemplary embodiment of the present invention, after injecting a blood sample through the injection base unit 150, the base unit and the injection base unit 150 which are connected to each other are separated to prevent the re-diffusion of the sample.

Figure 4:
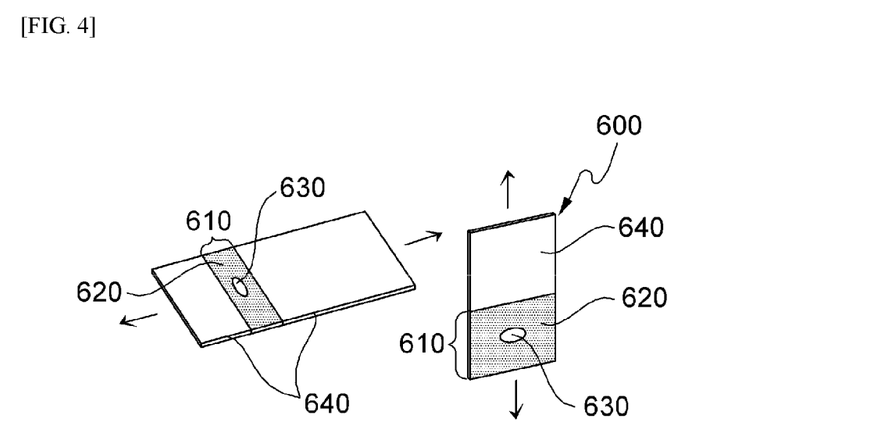
FIG. 4 illustrates a slip layer unit in a biological sample separation device according to another exemplary embodiment of the present invention

FIG. 4 additionally illustrates a slip layer unit 600 in addition to a biological sample separation device 10 of FIG.

2 according to an exemplary embodiment of the present invention. FIG. 4 will be described with reference to FIGS. 1 and 2.

FIG. 4 illustrates a slip layer unit 600 which may be additionally configured in the foldable base 100 in the biological sample separation device 10.

The slip layer unit 600 may include a slip layer base 610 to which a sample is adsorbed, a slip layer coating layer 620 which is located in at least partial area of the slip layer base 610 to prevent the adsorption of the sample, and a slip layer reservoir 630 which has an area defined by the slip layer coating layer 620 and adsorbs and stores the sample to be measured or provides a movement path. Further, a support 640 which serves as a handle when the slip layer unit 600 is inserted into or removed from the base 100 may be further included. The support 640 may be implemented by the same material as the base 100 or the slip layer unit 600 or plastic.

Figure 5:
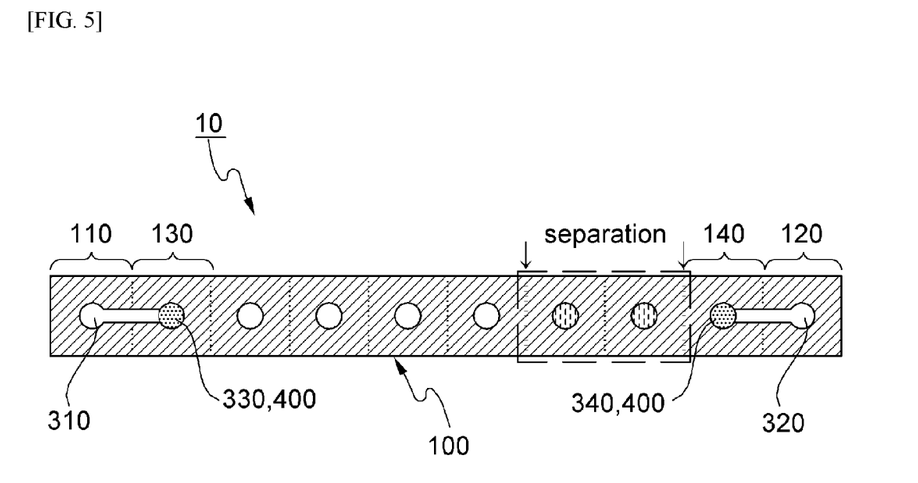
FIG. 5 illustrates concentration and separation areas of a biological sample separation device according to an exemplary embodiment of the present invention.

The slip layer unit 600 wets the slip layer reservoir 630 with the sample and is inserted into a specific section of the base 100 to perform the separation and concentration of the sample. Further, the slip layer unit 600 wets the reservoir with the sample or is wet with the sample through the injection base unit 150 to be inserted into the specific section of the base 100 and perform the separation and concentration to obtain a concentrated target material or a material to be separated in the specific section. FIG. 5 illustrates concentration and separation areas of a biological sample separation device according to an exemplary embodiment of the present invention. FIG. 5 will be described with reference to FIG. 2 as follows.

At least one base unit which is a basic unit of the base 100 is separated as needed to selectively collect the target material of the sample or the separation object.

The base 100 may be folded with a predetermined interval and the base units as the folded basic unit overlap each other. When a potential difference is generated at both ends of the base 100, the sample may be separated or concentrated through the overlapping reservoirs by electro osmosis flow (EOF) or electrophoresis (EP) and the mobility difference of the sample component. In this case, for one or more base units, a specific section is separated as needed to selectively obtain the target material or the separation object.

For example, albumin and globulin among the plasma components are protein components having the largest volume in the plasma and serve as a noise of a signal. Therefore, albumin and globulin are required to be separated. Therefore, as an exemplary embodiment of the present invention, when the separation is performed with the plasma as a sample to be processed, the plasma is directly injected into the reservoir or a separate reservoir is used to receive the plasma sample and the potential is applied to both ends of the base 100. In this case, the plasma component is separated and as illustrated in FIG. 5, the base unit in which the separated albumin or globulin are concentrated may be separated.

Figure 6A:
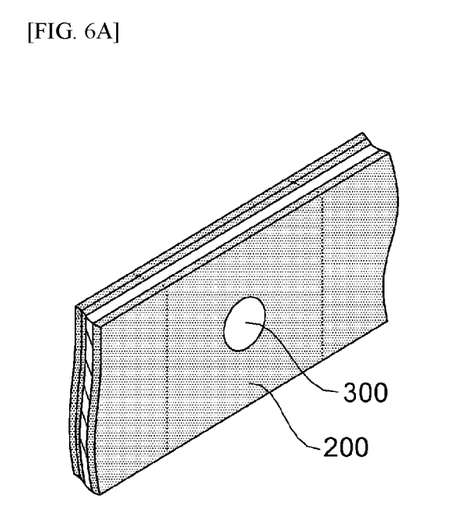
FIGS. 6A and 6B illustrate a coating layer of a biological sample separation device according to an exemplary embodiment of the present invention.
Figure 6B:
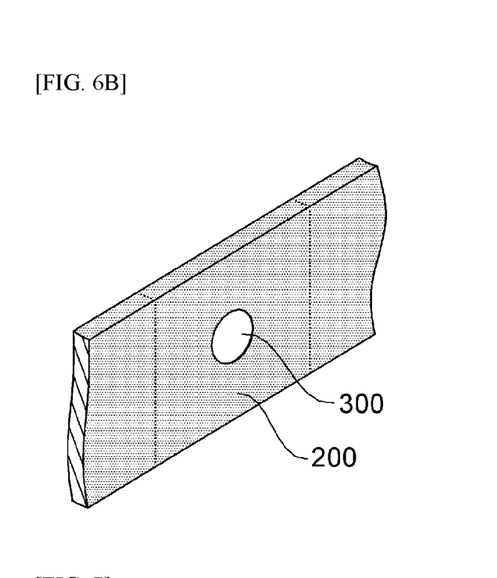

FIGS. 6A and 6B illustrate a forming method of a coating layer of a biological sample separation device according to an exemplary embodiment of the present invention.

The coating layer 200 includes a hydrophobic material for preventing the adsorption of the sample. A coating layer of the hydrophobic material having a predetermined pattern by the cutting which is a physical cutting method is formed and then attached onto both surfaces of the base 100 or formed by applying the hydrophobic material according to the pattern.

According to the exemplary embodiment of the present invention, the coating layer 200 is coupled to the base 100 to prevent the adsorption of the sample onto the base 100 and the sample may be stored or move through a reservoir channel which is the base 100 which is exposed without being coupled to the coating layer 200.

The coating layer 200 may be formed by cutting a pre-made film type material to have a desired pattern to be attached onto both ends of the base 100 or heated to be attached as illustrated in FIG. 6A or formed by applying the coating layer with a desired pattern or impregnating into the base 100. However, due to the characteristic of the present invention that the sample moves between the reservoirs 300, it is desirable to manufacture the coating layer by applying and impregnating the coating layer for the purpose of prevention of the loss of the sample.

Figure 7:
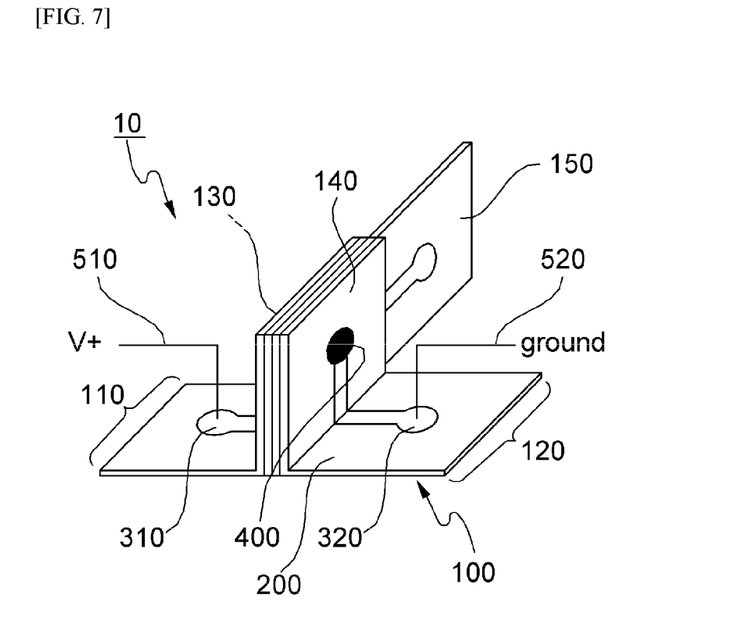
FIG. 7 illustrates a state in which a biological sample separation device according to an exemplary embodiment of the present invention is folded.

FIG. 7 illustrates a state in which a biological sample separation device 10 according to an exemplary embodiment of the present invention is folded. FIG. 7 will be described below.

The sample separation device 10 includes a base 100 provided such that a plurality of base units is folded and the folded structure is selectively unfolded, a coating layer 200 which is located in at least a partial area of the base unit to prevent the adsorption of the sample to be processed and separates a storage space or a movement path, a plurality of reservoirs 300 which has an area defined by the coating layer 200, is located in each base unit, at least partially adsorbs and stores a target material to be separated included in the sample to be measured or a separation object excluding the target material from the sample or provides a movement path, and a selective ion permeable layer 400 which at least partially overlaps at least some of reservoirs and selectively transmits the ion.

The sample separation device 10 includes the base 100 and in the base 100, the base units having a predetermined interval are folded to overlap each other. In this case, a first end base unit 110 and a second end base unit 120 do not overlap the other base units and serve as supports of the entire base 100. The coating layer 200 patterned to have a predetermined pattern is coupled to the base 100. In each base unit, a reservoir 300 in which the sample is stored or the sample moves may be located in each base unit as a base 100 which is exposed without being coupled to the coating layer.

In the folded base 100, the reservoirs 300 may be implemented to overlap each other and the sample may move between the overlapping reservoirs 300. Among reservoirs, a reservoir 300 located in the first end base unit 110 is a first end reservoir 510 and a reservoir 300 located in the second end base unit 120 is a second end reservoir 320. A first electrode 510 is connected to the first end reservoir 310 and a second electrode 520 is connected to the second end reservoir 320. According to the exemplary embodiment of the present invention, V+ is applied to the first electrode and the second electrode is grounded and the sample is separated using electro osmosis flow (EOF) and electrophoresis (EP) phenomenon.

A base unit adjacent to the first end base unit 110 is a third end base unit 130 and the third end reservoir 310 is located therein. A base unit adjacent to the second end base unit 120 is a fourth end base unit 140 and the fourth end reservoir 340 is located therein. A selective ion permeable membrane 400 which selectively transmits ions may be coupled to the third end reservoir 330 and the fourth end reservoir 340.

According to an exemplary embodiment of the present invention, the sample separation device 10 may further include a first electrode 510 connected to the first end reservoir 310 and a second electrode 520 connected to the second end reservoir 320.

According to the exemplary embodiment of the present invention, the sample separation device 10 may further include a first end reservoir 310 as a reservoir 300 which is located at one end of the base 100 and located in the first end base 110 serving as a support of the base 100, a second end reservoir 320 as a reservoir which is located at the other end of the base and located in the second end base 120 serving as a support of the base, a third end reservoir 330 which is a reservoir 300 which is located in the third end base unit 130 adjacent to the first end base unit 110 and connected to the first end reservoir 310 among the reservoirs and a fourth end reservoir 340 which is a reservoir 300 which is located in the fourth end base unit 140 adjacent to the second end base unit 120 and connected to the second end reservoir 320.

The sample separation device 10 may further include an injection base unit 150 which is directly connected to the base unit, rather than the first to fourth end base units 110, 120, 130, and 140 and at least partially located at the outside of the folded base 100, and injects the sample.

The coating layer 200 which prevents the adsorption of the sample or the buffer is at least partially applied or cut to be attached to the injection base unit 150. Further, as a base exposed without being coupled with the coating layer 200, a sample injection channel 155 which is exposed without being coupled with the injection reservoir 153 and the coating layer 200 to serve as a movement path of the sample to be processed which connects the reservoir of the connected base unit and the injection reservoir 153 may be located.

The injection base unit 150 has a purpose of injecting a sample to be processed or a buffer to wet the reservoir 300. As an exemplary embodiment of the present invention, after injecting a blood sample through the injection base unit 150, the base unit and the injection base unit 150 which are connected to each other are separated to prevent the re-diffusion of the sample.

As an exemplary embodiment of the present invention, the slip layer unit 600 which is independently provided from the base 100 may or may not wet the slip layer reservoir 630 with the sample and is inserted into a specific section of the folded base 100 and then the voltage is applied to the first electrode and the second electrode to perform the separation of the sample. The slip layer unit 600 is collected to use the sample which is concentrated or separated in the specific section.

As the contents of the present invention, when the voltage is applied to the sample separation device 100, an exemplary embodiment of the concentration through a selective ion permeable membrane is as follows.

For example, a blood sample is injected into the reservoirs 300, in an area where the reservoir 300 and the selective ion permeable layer 400 overlap, a blood fluid is in contact with the surface of the selective ion permeable membrane 400 so that induced charges having different properties are generated therebetween. As described above, a particular layer in which induced charges generated in the fluid are present is referred to as an electric double layer (EDL). In this case, when an external power is applied to the first end reservoir 310 and the second reservoir 320 disposed at both ends to generate a voltage difference, ions present in the fluid are attracted to an electrode having an opposite electric property of each ion by the electric field in accordance with the voltage difference. As described above, ions move between the reservoirs 300 according to their electrical properties to lead fluid particles together by the viscous force. Therefore, the entire fluid flows and the movement of the fluid is referred to as electro osmosis flow (EOF) and the movement of the ions is referred to as electrophoresis (EP).

The characteristics of the electrophoresis and the electro osmosis flow vary in the vicinity of the nano channel implemented as a selective ion permeable membrane (ipsm) so that the ion concentration polarization is generated. Therefore, in the reaction region of the reservoirs 300 overlapping the selective ion permeable membrane 400 serving as a nano channel, ion enrichment is generated at the negative electrode and ion depletion is generated at the positive electrode. In this case, the depletion zone may act as an electric barrier for charged protein by the low depletion ion concentration and a high electric field. As a result, the protein does not pass through the depletion zone and concentrated in front of the depletion zone. That is, the protein which is a target material is very quickly concentrated in front of the depletion zone in the reservoirs 300.

Figure 8A:
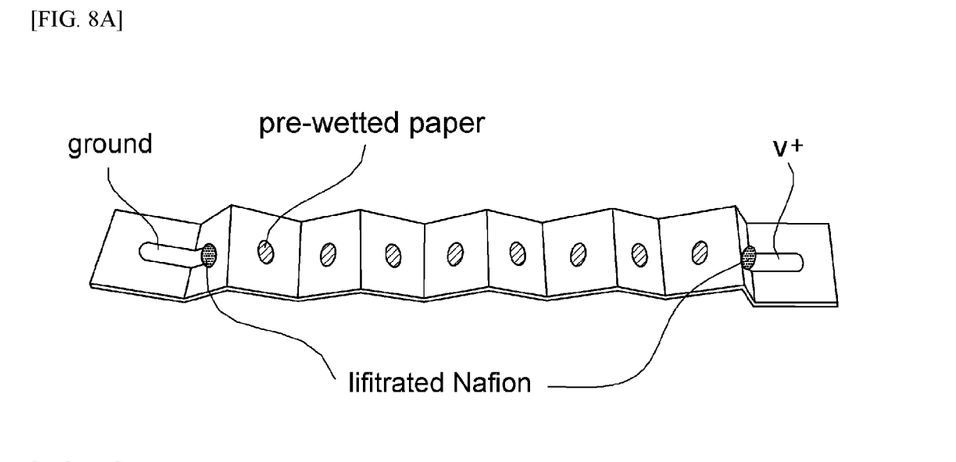
FIGS. 8A and 8B illustrate an experiment process and a result of a biological sample separation device according to an exemplary embodiment of the present invention.
Figure 8B:
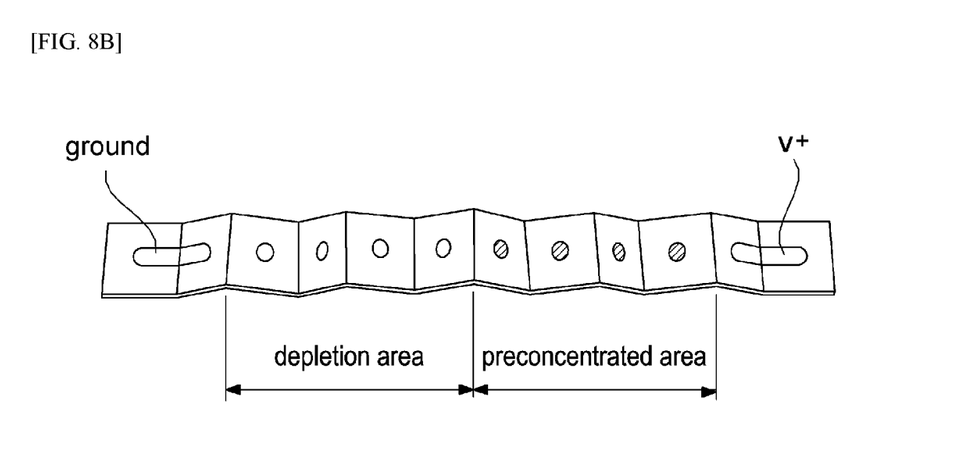

FIG. 8 illustrates an experiment process and a result using a sample separation device according to an exemplary embodiment of the present invention. FIG. 8 will be described with reference to FIG. 7 as follows.

FIG. 8A illustrates a state in which no voltage is applied. Referring to FIGS. 7 and 8A, as a sample to be processed, 1 ml of an orange G dye (1 mg/ml) and 1 ml of phosphate buffer saline (PBS) solution are injected into each reservoir 300 and the selective ion permeable membrane 400 is located in the third end reservoir 330 and the fourth end reservoir 340.

Figure 9:
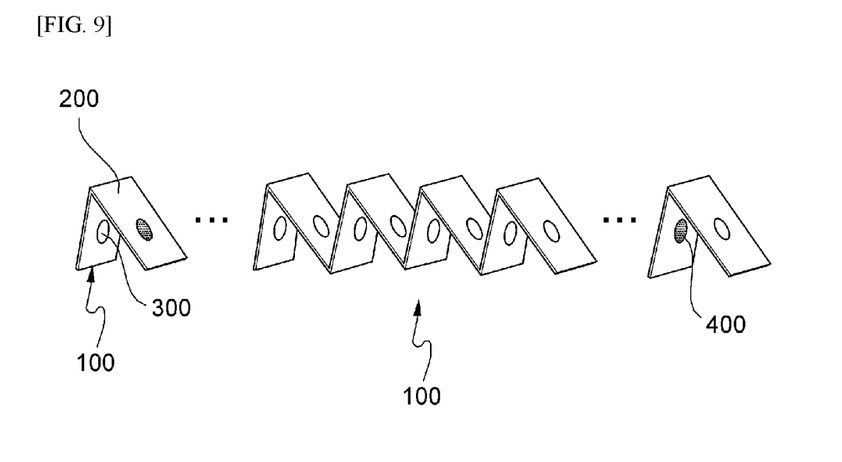
FIG. 9 illustrates a folding process of a biological sample separation device according to an exemplary embodiment of the present invention.

FIG. 8B illustrates a state in which a voltage is applied. Referring to FIGS. 7 and 8B, the base 100 is folded such that base units overlap to overlap the areas of the reservoirs 300 and then the first electrode 510 is connected to the first end reservoir 310 and the second electrode 520 is connected to the second end reservoir 320. Thereafter, the first electrode 510 is grounded and 100 V of voltage is applied to the second electrode 520 for 10 minutes and then the base 100 is unfolded. In this case, as the effect of the selective ion permeable membrane 400, ion concentration polarization (ICP) is generated. Therefore, the closer the base unit to which V+ is applied, the thicker the concentration of the sample. Further, the separation is generated such that the depletion area and the preconcentrated area of the sample are clearly distinguished. FIG. 9 illustrates a folding process of a biological sample separation device according to an exemplary embodiment of the present invention.

The base 100 may be provided to be folded in accordance with a predetermined interval in advance. In this case, the unit which is folded with a predetermined interval is defined as a base unit. As the folding method, as illustrated in FIG. 9, the base is folded such that the reservoirs 300 located in each base unit is in contact with the adjacent reservoir 300 by pleat fold. Each reservoir 300 may be implemented to have a circular shape as illustrated in the drawing and also implemented to have various shapes such as a triangular shape, a rectangular shape, and a pentagram. However, the shapes of the reservoirs 300 included in each base unit are not necessarily the same.

A position where a collection object is concentrated among the plurality of reservoirs may vary depending on an intensity of electric field, a length of the movement channel, a thickness of the base unit, and a size of micro pore. An origami-chip or vertical flow assay (VFAs) structure may reduce a reaction time as compared with the existing lateral flow assays (LFAs) and reduce line interference, and specifically remove hoot effect.

Specifically, a layer may be simply added in the middle of layer. That is, a plurality of reservoirs is formed in every layer or in one layer to selectively detect different targets.

Figure 10A:
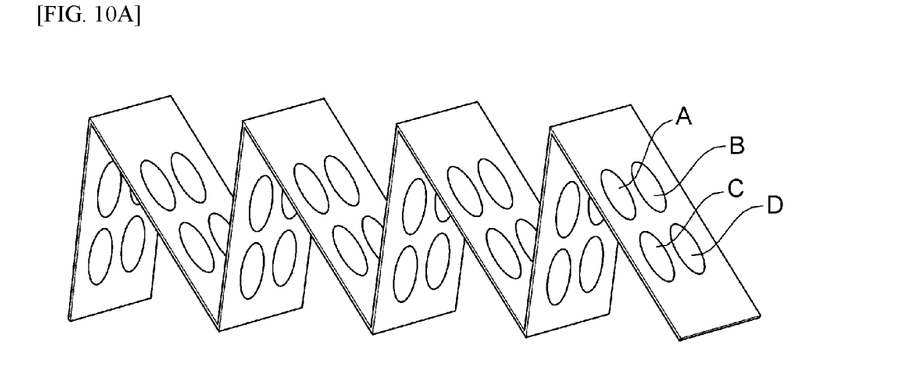
FIGS. 10A and 10B illustrate a biological sample separation device according to another exemplary embodiment of the present invention and a simulation result thereof.
Figure 10B:
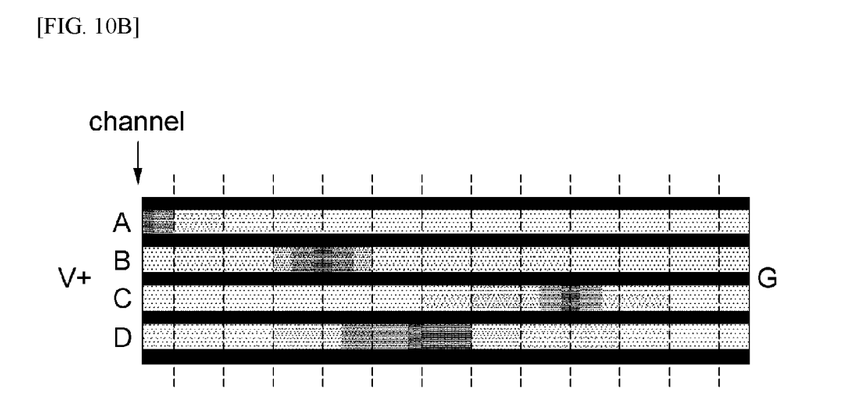

FIGS. 10A and 10B illustrate a biological sample separation device according to another exemplary embodiment of the present invention and a simulation result thereof. FIGS. 10A and 10B will be described with reference to FIGS. 1 to 9 as follows.

FIG. 10A illustrates a sample separation device according to an exemplary embodiment of the present invention. As an exemplary embodiment of the sample separation device 10 illustrated in FIGS. 1 to 9, a plurality of sample separation channels configured by a plurality of reservoirs which provides a movement path is provided. In the sample separation device 10, when the sample separation device 10 is folded with the interval of the base unit, the plurality of reservoirs 300 is adjacent to each other to form sample separation channels. In this case, as illustrated in FIG. 10A, each unit base unit includes the plurality of reservoirs 300 to form a plurality of sample separation channels and simultaneously separate and concentrate different samples. The sample separation device 10 illustrated in FIG. 10A is foldable and includes a sample separation channel A, a sample separation channel B, a sample separation channel C, and a sample separation channel D.

FIG. 10B illustrates a result of a simulation for different samples using the sample separation device 10 including a plurality of sample separation channels illustrated in FIG. 10A. When V+ voltage and a ground voltage are applied to both ends using the sample separation device 10 including the plurality of sample separation channels as illustrated in FIG. 10A, the sample is separated and concentrated and different separation and concentration results for different samples A to D are obtained. The dotted line indicates an unit interval with which the sample separation device is folded and corresponds to a base unit interval of the present invention.

Figure 11:
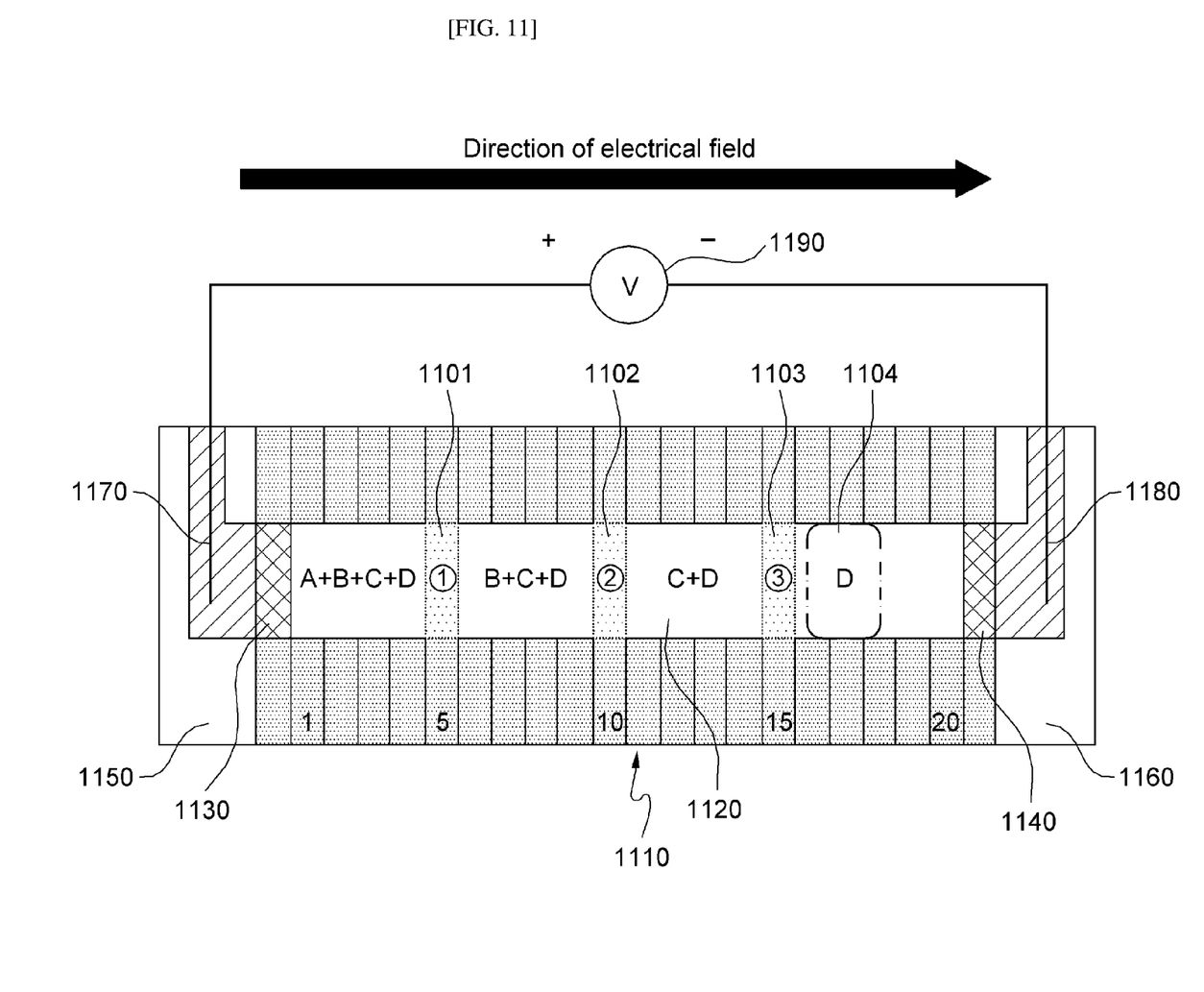
FIG. 11 is a front view of a biological sample separation device including a filter layer according to another exemplary embodiment of the present invention.

FIG. 11 is a front view of a biological sample separation device including a filter layer according to another exemplary embodiment of the present invention. The sample separation device includes a base, a coating layer, a plurality of reservoirs, a selective ion permeable layer, and a filter layer.

The base includes a plurality of base units and the plurality of base units 1110 is folded. At least some of the plurality of base units may be separated.

The coating layer is located in at least a part of the base to prevent the adsorption of the sample and divide a storage space or a movement path.

The plurality of reservoirs has an area set by the coating layer and located in the plurality of base units. The plurality of reservoirs may store or move a collection object to be separated from the sample. Alternatively, the plurality of reservoirs may store or move a separation object rather than the collection object included in the sample. A first end base unit 1150 located at one end of the base includes a first end reservoir and a second end base unit 1160 located at the other end of the base includes a second end reservoir. The sample separation device may further include a first electrode connected to the first end base unit and a second electrode connected to the second end base unit.

The selective ion permeable layer is coupled to some reservoirs among the plurality of reservoirs to selectively transmit ions. A plurality of selective ion permeable layers may be provided. The plurality of selective ion permeable layers 1130 and 1140 may be spaced apart from each other with a predetermined distance along a movement direction of the collection object. The plurality of selective ion permeable layers is connected to the first end reservoir and the second end reservoir, respectively.

An electric field 1190 is applied to the plurality of selective ion permeable layers to concentrate the collection object in the middle of the movement path of the collection object formed by folding the plurality of base units. The sample separation device forms a concentration area 1104 in the movement path of the collection object formed by folding the plurality of base units, that is, the sample separation channel.

The filter layers 1101 to 1103 are located in the middle of the movement path 1120 of the collection object formed by folding the plurality of base units 1110 to filter the separation object. The filter layer includes a porous membrane and a size of the micro pore in the filter layer may be set in advance. A size of the micro pore of the filter layer is larger than a size of the collection object and smaller than a size of the separation object.

The sample separation device inserts the filter layer having a predetermined size into the sample separation channel or forms a sample separation channel which is folded to be sequentially separated, depending on the size of the collection object. That is, the sample separation device may separate the collection object and the selection object.

The filter layer is directly connected to a base unit which is not located at the end, among the plurality of base units and a filter layer is inserted in the middle of the movement path of the collection object during a process of folding the plurality of base units. For example, like the injection base unit 150 illustrated in FIG. 3, the filter layer may be connected to the base.

In the meantime, like the slip layer unit illustrated in FIG. 4, the filter layer may be formed to be inserted in the middle of the overlapping base units. The filter layer may have a handle to be easily inserted.

The number of filter layers is plural and the plurality of filter layers is located on the movement path of the collection object formed by folding the plurality of base units to sequentially separate two or more separation objects.

The filter layer may further include a display unit which displays an intensity of the pressure which is applied to the filter layer or a size of micro pore.

A position where the collection object is concentrated may vary depending on an intensity of the electric field, a length of the movement channel, a thickness of the base unit, a size of micro pore of the base, a size of micro pore of the filter layer, and the position of the filter layer. The sample separation device may separate the separation object on the movement path of the collection object in advance to adjust the position where the collection object is concentrated.

As a method of compressing a membrane (for example, the base unit or the filter layer), simply, a hand press machine may be used. A membrane fixed onto a sensor which measures an intensity of the pressure such as a load cell is compressed. The pressure is checked by a pressure indicator connected to the load cell and the physical change of the membrane in accordance with the intensity of the pressure may be observed.

Figure 12:
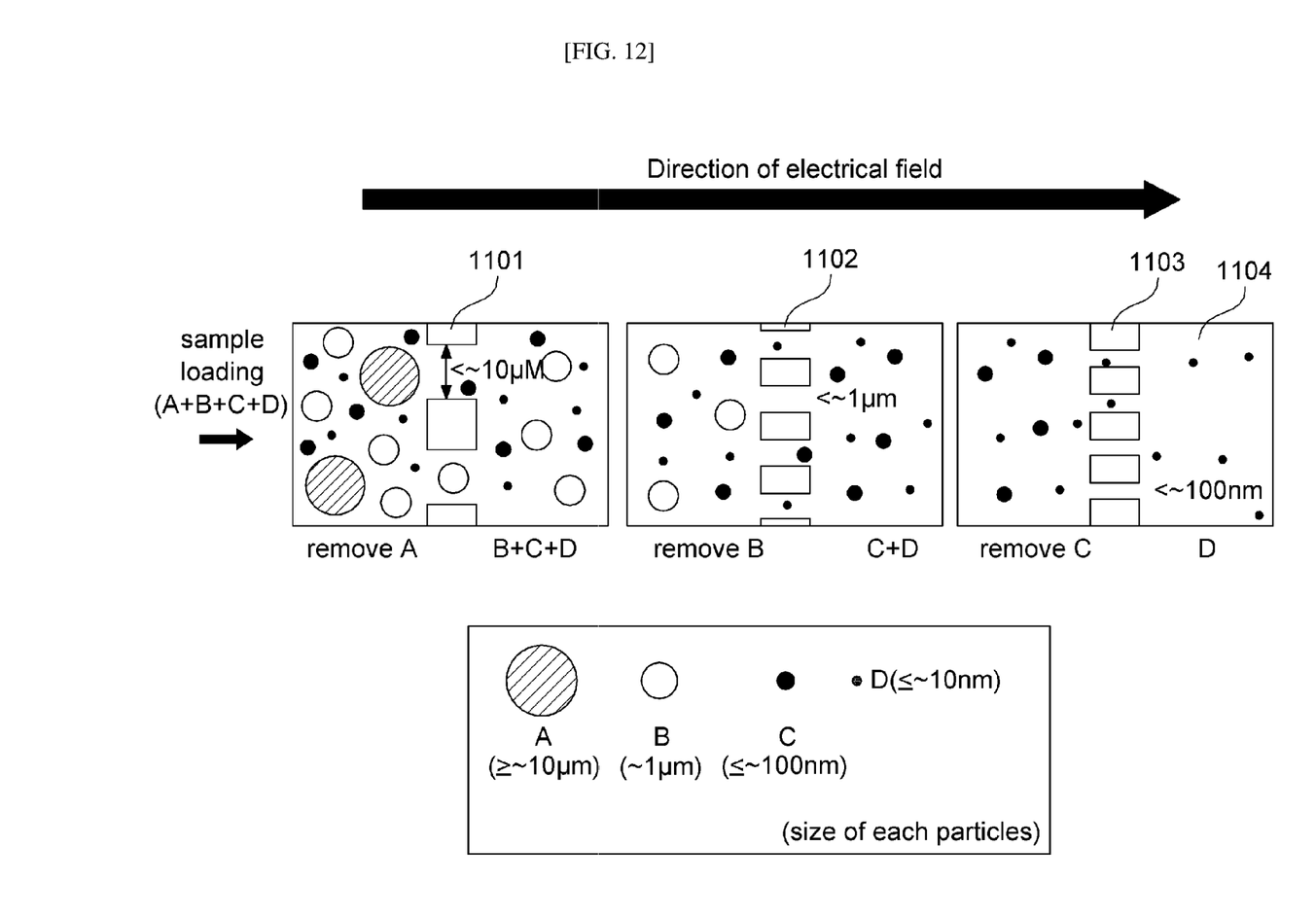
FIG. 12 illustrates an operation of a filter layer of a biological sample separation device according to another exemplary embodiment of the present invention.

The pressure indicator is a device which converts an analog value of a pressure intensity into a digital signal. The pressure indicator represents the change of the thickness of the paper and the pore size in accordance with the intensity of the pressure which is applied to the paper. It is identified that the size of the micro pore is surely reduced in accordance with the intensity of the pressure. For example, the micro pore of the compressed paper may be analyzed by the scanning electron microscope (SEM). FIG. 12 illustrates an operation of a filter layer of a biological sample separation device according to another exemplary embodiment of the present invention.

Referring to FIG. 12, a plurality of filter layers and a concentrated area may be formed in the middle of a separation channel of a biological sample separation device. For example, the plurality of filter layers may form a first filter layer 1101, a second filter layer 1102, a third filter layer 1103, and a concentrated area 1104. The plurality of filter layers 1101, 1102, and 1103 may have different pore sizes using a mechanical or physical method or commercialized different membranes.

When an electric field is applied from the left to the right, the target materials generally move from the left to the right. That is, the plurality of objects is concentrated by applying an electric field to the selective ion permeable layer and the plurality of objects passes through some filter layers or does not pass through the other filter layer to be separated.

When a pore size of the first filter layer 1101 is 10 μm, a material A larger than 10 μm is filtered, when a pore size of the second filter layer 1102 is 1 μm, a material B larger than 1 μm is filtered, when a pore size of the third filter layer 1103 is 100 nm, a material C larger than 100 nm is filtered, and finally, a material D is concentrated to form a concentrated area 1104. The materials A, B, and C are gradually separated by the membranes having different pore sizes and as a result, only particles D having the smallest size (for example, exosomes) may be separated. As a result, only a pure D target is separated and concentrated. The separation objects A, B, and C are filtered on the separation channel using the filter layers so that a total number of base units may be reduced, the position of the concentrated area may be adjusted, and the concentration time may be reduced.

The base unit including the concentrated collection object may include a perforated line in which small holes are formed in advance to be easily separated from the base.

The present embodiments are provided to explain the technical spirit of the present embodiment and the scope of the technical spirit of the present embodiment is not limited by these embodiments. The protection scope of the present embodiments should be interpreted based on the following appended claims and it should be appreciated that all technical spirits included within a range equivalent thereto are included in the protection scope of the present embodiments.

The invention claimed is:

1. A sample separation device, comprising:
a base which includes a plurality of base units and is formed such that the plurality of base units is folded;
a coating layer which is located in at least a partial area of the base to prevent the adsorption of a sample and separate a storage space or a movement path;
a plurality of reservoirs which has an area set by a collating layer, is located in the plurality of base units, and stores or moves a collection object to be separated from the sample or a separation object excluding the collection object included in the sample;
a selective ion permeable layer which is coupled to some reservoirs of the plurality of reservoirs to selectively transmit ions; and
a plurality of filter layers located in a middle of a movement path of the collection object formed by the plurality of base units to filter the separation object,
wherein when an electric field is applied to the selective ion permeable layer in a folded state of the base, ion concentration polarization is generated, and a depletion area and a concentrated area are formed respectively in some base units among the plurality of base units,
wherein each of the plurality of filter layers comprises a porous membrane having a distinct pore size, and
wherein the plurality of filter layers are arranged in the movement path of the collection object to reduce a number of base units that the collection object passes through and to adjust a position of some base units that the concentrated area is formed, among the plurality of base units, the collection object being concentrated in the concentrated area.

2. The sample separation device of claim 1, wherein a first end base unit located at a first end of the base includes a first end reservoir and a second end base unit located at a second end of the base includes a second end reservoir, and the first end reservoir and the second end reservoir are connected to the selective ion permeable layer, the first end and the second end being opposite ends of the base.

3. The sample separation device of claim 2, wherein the selective ion permeable layer is located in a third end reservoir which is a reservoir located in a third end base unit adjacent to the first end base unit and a fourth end reservoir which is a reservoir located in a fourth end base unit adjacent to the second end base unit.

4. The sample separation device of claim 1, further comprising:
an injection base unit which is directly connected to a base unit, which is not located at an end of the base, among the plurality of base units and at least partially located at outside when the base is folded, and injects the sample.

5. The sample separation device of claim 4, further comprising:
on at least one surface of the injection base unit,
an injection base unit coating layer which is located in at least a partial area of the injection base unit and prevents the adsorption of a sample to be processed and separates a storage space or a movement path;
an injection reservoir which is connected to a reservoir included in the base unit which is not located at an end of the base and is wet to inject the sample to be processed; and
a sample injection channel which has an area divided by the coating layer and serves as a movement path of the sample to be processed, the sample injection channel connecting the reservoir included in the base unit which is not located at an end of the base and the injection reservoir to each other.

6. The sample separation device of claim 1, wherein the base includes a porous membrane.

7. The sample separation device of claim 1, further comprising:
a slip layer unit which includes a slip layer base, a slip layer coating layer located in at least a partial area of the slip layer base, and a slip layer reservoir which has an area defined by the slip layer coating layer and at least partially adsorbs and stores the sample to be measured or provides a movement path and is provided to be inserted or removed between at least some of base units included in the base,
wherein the slip layer reservoir is wet with a sample to be processed or a conductive liquid to inject a sample.

8. The sample separation device of claim 1, wherein the plurality of reservoirs is wet with a sample to be processed or a conductive liquid.

9. The sample separation device of claim 1, wherein at least one base unit is separated as needed to selectively collect a target material of the sample or the separation object.

10. The sample separation device of claim 1, wherein the coating layer includes a hydrophobic material for preventing the adsorption of the sample, and is attached onto both surfaces of the base after forming the coating layer of the hydrophobic material having a predetermined pattern by a cutting which is a physical cutting method or forming the coating layer by applying the hydrophobic material according to the predetermined pattern.

11. The sample separation device of claim 1, wherein a size of micro pores in each of the plurality of filter layers is larger than a size of the collection object and is smaller than a size of the separation object.

12. The sample separation device of claim 11, wherein the size of micro pores is adjusted by compressing one or more filter layers and the one or more filter layers further include a display unit which displays an intensity of a pressure applied to the one or more filter layers or the size of micro pores.

13. The sample separation device of claim 1, wherein the plurality of filter layers is located on the movement path of the collection object formed by the plurality of base units to sequentially separate two or more separation objects.

14. The sample separation device of claim 1, wherein each of the plurality of filter layers is directly connected to a base unit which is not located at an end of the base among the plurality of base units, and the plurality of filter layers are inserted in the middle of the movement path of the collection object during a process of folding the plurality of base units.

\* \* \* \* \*